US00PP27025P3

(12) United States Plant Patent
Olesen

(10) Patent No.: US PP27,025 P3
(45) Date of Patent: Aug. 9, 2016

(54) COMPACT FLORIBUNDA ROSE PLANT NAMED 'POULPAL058'

(50) Latin Name: ***Rosa* hybrid**
Varietal Denomination: Poulpal058

(71) Applicant: Mogens Nyegaard Olesen, Fredensborg (DK)

(72) Inventor: Mogens Nyegaard Olesen, Fredensborg (DK)

(73) Assignee: POULSEN ROSER A/S, Fredensborg (DK)

( * ) Notice: Subject to any disclaimer, the term of this patent is extended or adjusted under 35 U.S.C. 154(b) by 0 days.

(21) Appl. No.: 14/121,273

(22) Filed: Aug. 15, 2014

(65) Prior Publication Data

US 2016/0050816 P1 Feb. 18, 2016

(51) Int. Cl.
*A01H 5/02* (2006.01)

(52) U.S. Cl.
USPC ..... Plt./146

(58) Field of Classification Search
USPC ..... Plt./146
CPC ..... A01H 5/0222; A01H 5/0216
See application file for complete search history.

(56) References Cited

PUBLICATIONS http://www.poulsenroser.dk/media/73602/PATIOHIT-Outdoor-2013_LR_Poulsen-Roser.pdf; 2012; 1 page.*

* cited by examiner

*Primary Examiner* — Kent L Bell

(57) ABSTRACT

A new garden rose plant of the Compact Floribunda class which has abundant, orange red flowers and attractive foliage. This new and distinct variety has shown to be uniform and stable in the resulting generations from asexual propagation.

2 Drawing Sheets

Botanical designation: *Rosa* hybrid.
Variety denomination: 'Poulpal058'.

SUMMARY OF THE INVENTION

The present invention constitutes a new and distinct variety of garden rose plant which originated from a controlled crossing between the female seed parent, an unnamed seedling, and the male pollen parent, also an unnamed seedling.

The two parents were crossed during the summer of 2004 and the resulting seeds were planted in a controlled environment in Fredensborg, Denmark. The new variety, named 'Poulpal058', originated as a single seedling from the stated cross.

The new variety may be distinguished from its male pollen parent and female seed parent by the following characteristics. The female seed parent and the male pollen parent have red flowers while the new variety has orange red flowers.

The objective of the hybridization of this rose variety was to create a new and distinct variety for garden use with unique qualities, such as:

1. Uniform and abundant orange red flowers;
2. Vigorous, but very compact growth when propagated both as a budded rose and on its own roots;
3. Exceptional disease resistance.

This combination of qualities is not present in previously available commercial cultivars of this type, known to the inventor, and distinguish 'Poulpal058' from all other varieties of which we are aware.

As part of the rose development program, Mogens N. Olesen germinated the seeds from the aforementioned hybridization during winter of 2004 and conducted evaluations on the resulting seedlings in a controlled environment in Fredensborg, Denmark. 'Poulpal058' was selected in the spring of 2005 by the inventor as a single plant from the progeny of the aforementioned hybridization.

Asexual reproduction of 'Poulpal058' by traditional budding and rooted cuttings was first done by Mogens N. Olesen in the nursery in Fredensborg, Denmark in July, 2005. This initial and other subsequent asexual propagations conducted in controlled environments have demonstrated that the characteristics of 'Poulpal058' are true to type and are transmitted from one generation to the next.

DESCRIPTION OF THE DRAWING

The accompanying color illustrations show as true as is reasonably possible to obtain in color photographs of this type, the typical characteristics of the buds, flowers, leaves, and stems, of 'Poulpal058'.

Specifically illustrated in FIG. 1 are flowers at various stages of development, flower in parts, FIG. 2 are flower buds, leaves, and stems. Plants shown are 2 years of age.

DETAILED DESCRIPTION OF THE VARIETY

Figure 1:
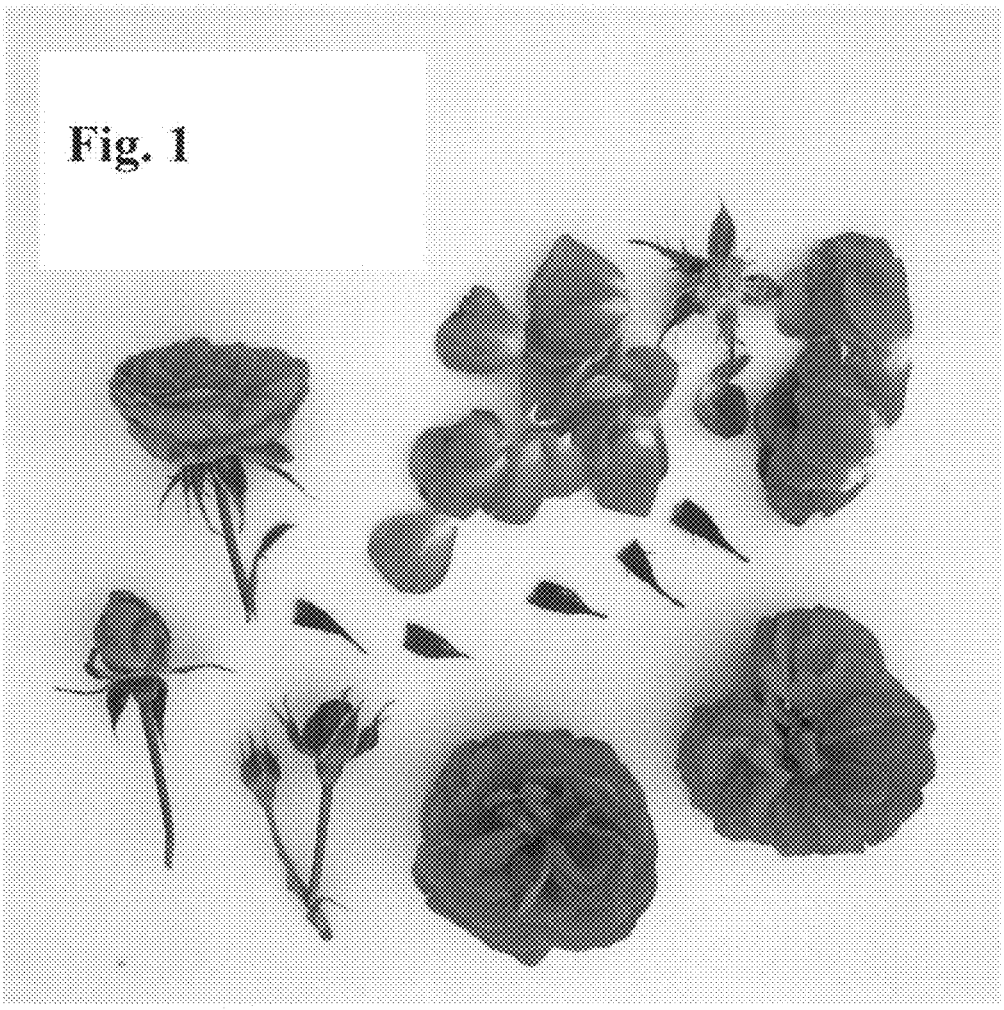
Figure 2:
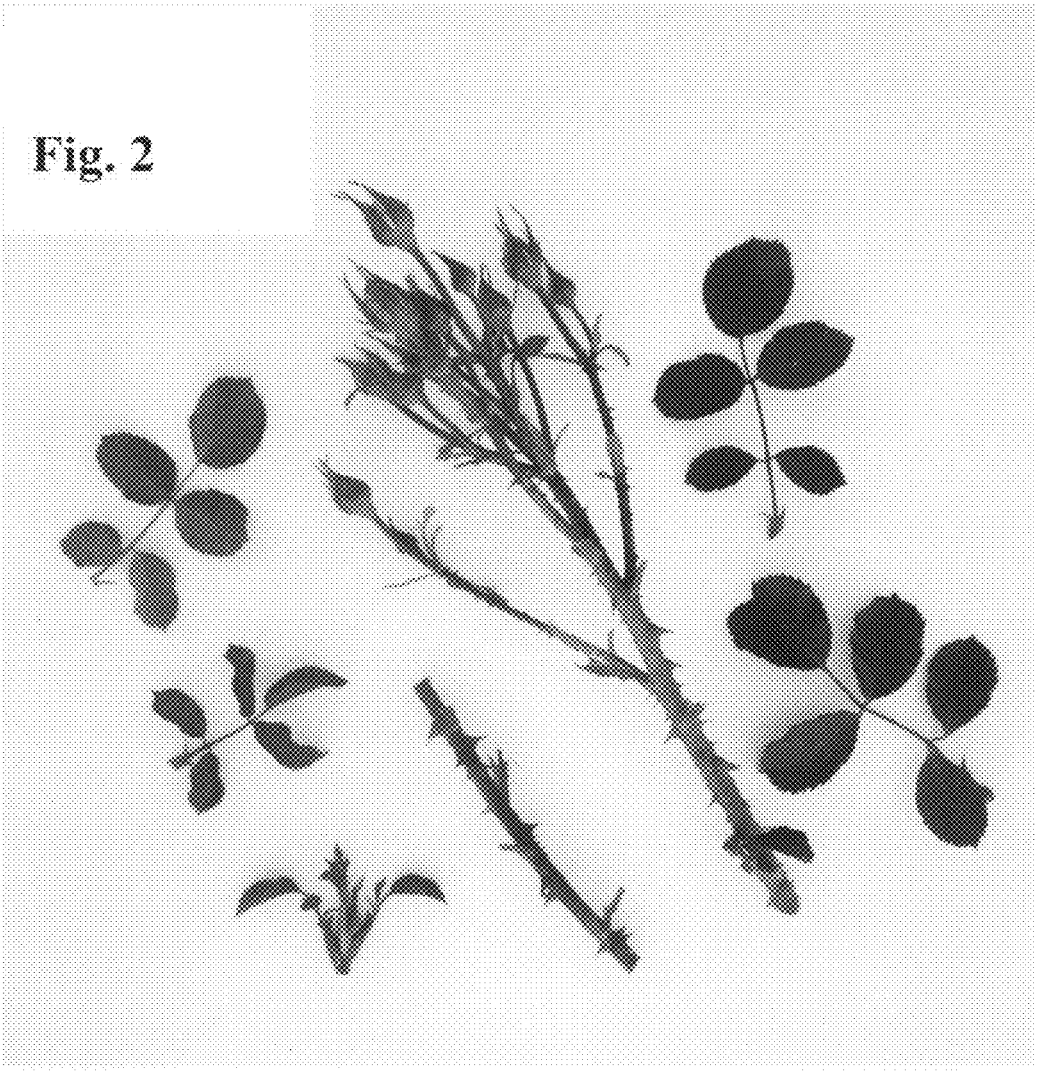

The following is a description of 'Poulpal058', as observed in its growth in a field nursery in Marion County, Oreg. Observed plants are 2 years of age, and were grown on their own roots. Color references are made using The Royal Horticultural Society (London, England) Colour Chart, 2001, except where common terms of color are used.

For a comparison, several physical characteristics of the rose variety 'Poulgrad', U.S. Plant Pat. No. 11,610 are compared to 'Poulpal058' in Chart 1.

CHART 1

| | 'Poulpal058' | 'Poulgrad' |
|---|---|---|
| Petal Count | 50 to 60 | 25 to 30 |
| Flower Diameter | 70 mm | 55 mm |
| General Tonality of Flower Color | Red Group 40A | Red Group 53A-46A |

FLOWER AND FLOWER BUD

Blooming habit: Continuous.

Flower bud:

*Size*.—Upon opening, 25 mm in length from base of receptacle to end of bud. Bud diameter is 15 mm.

*Bud form*.—Urceolate.

*Bud color*.—As sepals divide petals are Orange-Red Group N34A and Red Group 50B.

*Sepal inner surface*.—Color: Greyed-Orange Group 175A. Surface: Smooth and pubescent.

*Sepal outer surface*.—Color: Greyed-Purple Group 183A with intonations of Yellow-Green Group 144A. Texture: Smooth.

*Sepal shape*.—Apex: Cirrhose. Base: Flat at union with receptacle.

*Sepal margin*.—Margins have weak moderate foliaceous appendages on three of the five sepals.

*Sepal size*.—30 mm long by 10 mm wide.

*Receptacle*.—Texture: Smooth. Size: 9 mm in height by 8 mm wide. Color: Yellow-Green Group 144A. Anthocyanic pigments the color of Greyed-Orange Group 176B observed. Shape: Campanulate.

*Pedicel*.—Surface: Smooth. Length: 40 mm. Diameter: 3 mm on average. Color: Yellow-Green Group 144A. Anthocyanic pigments the color of Greyed-Orange Group 176B observed. Strength: Strong.

*Peduncle*.—Length: 30 to 80 mm. Texture: Small prickles. Diameter: 4 mm. Color: Greyed-Purple Group 183B.

Flower bud development: Flower buds are borne in clusters of about 15 flower buds per stem, resembling a corymb.

Flower bloom:

*Fragrance*.—Light floral scent.

*Duration*.—The blooms have a duration on the plant of approximately 7 to 10 days. Petals fall cleanly away from plant after flowers have fully matured.

*Size*.—Flower diameter is 70 mm when open. Flower depth is 30 mm.

*Flower shape*.—General shape is a rosette.

*Shape of flower, side view*.—The upper portion is flat. Underneath is a flattened convex.

Petalage: Under normal conditions, flowers have 50 to 60 petals total, 7 of which are petaloids.

General tonality of flower: Open flowers are Red Group 40A.

Petal color:

*Upon opening, outer and inner petals*.—Upper surface: Red Group 40A. Lower surface: Red Group 52A, splashed with White Group N155D.

*After opening, outer petals*.—Upper surface: Red Group 40A. Lower surface: Red Group 52A, splashed with Red Group 52B.

*After opening, inner petals*.—Upper surface: Orange-Red Group 43A. Lower surface: Red Group 52A, splashed with Red Group 52B.

Petals:

*Petal reflex*.—Moderate to strong reflex. Lateral fold.

*Margin*.—Entire and uniform. Moderate undulations of margin observed.

*Shape*.—Apex shape: Rounded. Base shape: Acute.

*Size*.—38 mm (l) 32 mm (w).

*Texture*.—Smooth.

*Thickness*.—Average.

Petaloids:

*Size*.—25 mm (l) by 15 mm (w).

*Quantity*.—About 7.

*Shape*.—Crescent shaped.

*Color*.—Red Group 52A underneath, Red Group 40A above. Yellow Group 2B at the base of the upper side.

Reproductive organs:

*Pollen*.—None observed.

*Anthers*.—Size: 3 mm in length. Color: Greyed-Yellow Group 162B. Quantity: 30 on average.

*Filaments*.—Color: Yellow Group 9C with intonations of Red Group 42D. Length: 5 mm.

*Pistils*.—Length: 5 mm. Quantity: 20 on average.

*Stigmas*.—Color: Yellow-Green Group 145D.

*Styles*.—Color: Yellow-Green Group 145D.

*Location of stigmas*.—Level relative to the length of the filaments and the height of the anthers.

*Hips*.—None Observed.

PLANT

Plant growth: Upright, bushy. Plants are 40 cm in height, and 40 cm wide.

Stems:

*Color*.—Juvenile growth: Yellow-Green Group 146B with strong intonations of Greyed-Red Group 178A. Mature growth: Yellow-Green Group 146B.

*Length*.—On average, canes are 15 cm from the base of the plant to the flowering portion.

*Diameter*.—9 mm.

*Internodes*.—On mature canes, there is an average distance of 32 mm between nodes.

*Surface texture*.—Young wood: Small prickles. Older wood: Small prickles.

Long prickles:

*Incidence*.—12 prickles per 10 cm of stem.

*Size*.—Average length of prickles on mature stems is 9 mm.

*Shape*.—Upper portion is linear. Lower portion is concave.

*Color*.—Juvenile prickles: Greyed-Purple Group 183A. Mature prickles: Yellow-Green Group 144C.

Plant foliage:

*Compound leaf*.—130 mm (l)×90 (w).

*Quantity*.—3 leaves per 10 cm of stem on average.

*Color of juvenile foliage*.—Upper side: Greyed-Purple Group 183A. Lower side: Greyed-Purple Group 183A.

*Color of mature foliage*.—Upper side: Yellow-Green Group 147A. Lower side: Yellow-Green Group 146A.

Plant leaves and leaflets:

*Stipules*.—Size: 25 mm in length. Quantity: 2 per compound leaf. Shape: Linear, slightly broad based with outward extending apices. Margins: Finely serrated. Color: Yellow-Green Group 146B.

*Petiole*.—Length: 25 mm. Diameter: 1 to 2 mm. Upper surface: Color: Yellow-Green Group 146B with intonations of Greyed-Red Group 182B. Lower surface: Color: Yellow-Green Group 144A.

*Rachis*.—Length: 50 mm. Upper surface: Color: Yellow-Green Group 146B with intonations of Greyed-Red Group 182B. Lower surface: Color: Yellow-Green Group 144A.

*Leaflet*.—Quantity: Normal number of leaflets leaves in middle of the stem is 5 leaflets. Margins: Serrated. Size: Average size of the terminal leaflet on normal leaves is 42 mm in length by 31 mm wide. Shape: Generally rounded. Base: Rounded. Apex: Mucronate. Texture: Smooth. Thickness: Average. Arrangement: Odd pinnate. Venation: Reticulate. Glossiness: Glossy.

Disease resistance: Above average resistance to powdery and downy mildew, rust, black spot, and *Botrytis* under normal growing conditions.

Cold hardiness: The variety is tolerant to USDA Cold Hardiness Zone 6.

Heat tolerance: The variety has been found to be suitable for climate conditions found in the American Horticulture Society heat zone 7.

The invention claimed is:

1. A new and distinct variety of rose plant of the Compact Floribunda rose class named 'Poulpal058', substantially as illustrated and described herein, due to its abundant orange red flowers, disease resistance, and extended period of bloom.

* * * * *